United States Patent
Yoon et al.

(10) Patent No.: US 9,458,131 B2
(45) Date of Patent: Oct. 4, 2016

(54) COMPOUNDS AND COMPOSITIONS USED TO EPIGENETICALLY TRANSFORM CELLS AND METHODS RELATED THERETO

(71) Applicants: Young-Sup Yoon, Atlanta, GA (US); Xiaodong Cheng, Decatur, GA (US); Ji Woong Han, Decatur, GA (US); Antonello Mai, Rome (IT)

(72) Inventors: Young-Sup Yoon, Atlanta, GA (US); Xiaodong Cheng, Decatur, GA (US); Ji Woong Han, Decatur, GA (US); Antonello Mai, Rome (IT)

(73) Assignee: Emory University, Atlanta, GA (US)

( * ) Notice: Subject to any disclaimer, the term of this patent is extended or adjusted under 35 U.S.C. 154(b) by 156 days.

(21) Appl. No.: 14/356,024

(22) PCT Filed: Nov. 8, 2012

(86) PCT No.: PCT/US2012/064066
§ 371 (c)(1),
(2) Date: May 2, 2014

(87) PCT Pub. No.: WO2013/070852
PCT Pub. Date: May 16, 2013

(65) Prior Publication Data
US 2014/0294764 A1    Oct. 2, 2014

Related U.S. Application Data

(60) Provisional application No. 61/556,895, filed on Nov. 8, 2011.

(51) Int. Cl.

| | | |
|---|---|---|
| C07D 239/72 | (2006.01) |
| C07D 211/08 | (2006.01) |
| C07D 211/56 | (2006.01) |
| C07D 401/12 | (2006.01) |
| A61K 31/517 | (2006.01) |
| A61K 45/06 | (2006.01) |
| A61K 31/5377 | (2006.01) |
| A61K 31/541 | (2006.01) |
| A61K 31/55 | (2006.01) |
| A61K 31/551 | (2006.01) |
| C07D 401/14 | (2006.01) |

(52) U.S. Cl.
CPC .......... *C07D 401/12* (2013.01); *A61K 31/517* (2013.01); *A61K 31/5377* (2013.01); *A61K 31/541* (2013.01); *A61K 31/55* (2013.01); *A61K 31/551* (2013.01); *A61K 45/06* (2013.01); *C07D 401/14* (2013.01)

(58) Field of Classification Search
None
See application file for complete search history.

(56) References Cited

U.S. PATENT DOCUMENTS 3,956,495 A    5/1976    Lacefield

FOREIGN PATENT DOCUMENTS

| IN | 2008KO01784 | | 4/2010 |
| WO | WO 0125218 A1 | * | 4/2001 |
| WO | 2004030672 | | 4/2004 |
| WO | 2004078733 | | 9/2004 |
| WO | 2009143421 | | 11/2009 |

OTHER PUBLICATIONS

Shaaban et al. Chemistry & Biology 2007 (14) 242-244 published Mar. 2007.*
Liu et al. J. Med. Chem. 2009 (52) 7950-7953 published Nov. 5, 2009.*
Shi et al. Cell Stem Cell 2008 (3) 568-574.*
Huangfu et al. Nature Biotechnology 2008 (26) 795-797.*
Park et al. Nature 2008 (45) 141-147.*
Krueger et al. The International Journal of Developmental Biology 2010 (54) 1545-1564.*
Telugu et al. The International Journal of Developmental Biology 2010 (54) 1703-1711.*
Chang et al. "Structural basis for G9a-like protein lysine methyltransferase inhibition by BIX-01294" Nat Struct Mol Biol., 2009; 16(3): 312-317.
Doi et al. "Differential methylation of tissue- and cancer-specific CpG island shores distinguishes human induced pluripotent stem cells, embryonic stem cells and fibroblasts" Nature Genetics, 2009; 41: 1350-1353.
Han et al. "Abstract 9595: Generation of Transgene-Free Induced Pluripotent Stem Cells from Fibroblasts by Small Molecule Chemicals" Circulation, 2011; 124: A9595.
Huangfu et al. "Induction of pluripotent stem cells by defined factors is greatly improved by small-molecule compounds" Nat Biotechnol, 2008; 26(7): 795-797.
Imamura et al. "Transcriptional repression and DNA hypermethylation of a small set of ES cell marker genes in male germline stem cells" BMC Developmental Biology, 2006; 6: 34.

(Continued)

*Primary Examiner* — Jeffrey S Lundgren
*Assistant Examiner* — Michael Schmitt
(74) *Attorney, Agent, or Firm* — Emory Patent Group

(57) ABSTRACT

This disclosure relates to compounds, compositions and methods of epigenetically transforming cells. In certain embodiments, the disclosure relates to methods of generating epigenetically altered cells comprising mixing isolated cells with compositions disclosed herein under conditions such that epigenetically altered cells are formed. In certain embodiments, the disclosure contemplates inducing cells, such as adult somatic cells or cells that are not naturally pluripotent, into cells with chemically induce pluripotency. In certain embodiments, the disclosure contemplates certain compounds disclosed herein, compounds disclosed herein optionally substituted with one or more substituents, derivatives, or salts thereof, for these purposes.

11 Claims, 5 Drawing Sheets

(56) References Cited

OTHER PUBLICATIONS

Krawetz et al. "Human embryonic stem cells: caught between a ROCK inhibitor and a hard place" Bioessay,. Mar. 2009; 31(3): 336-343.

Okita et al. "Generation of germline-competent induced pluripotent stem cells" Nature, Jul. 19, 2007; 448: 313-317.

Polychronopoulos et al. "Structural Basis for the Synthesis of Indirubins as Potent and Selective Inhibitors of Glycogen Synthase Kinase-3 and Cyclin-Dependent Kinases" J. Med. Chem., 2004; 47: 935-946.

Shaaban et al. "Reprogramming the Histone Code" Chemistry & Biology, 2007; 14: 242.

Shi et al. "A Combined Chemical and Genetic Approach for the Generation of Induced Pluripotent Stem Cells" Cell Stem Cell, 2008; 2: 525-528.

Takahashi et al. "Induction of pluripotent stem cells from mouse embryonic and adult fibroblast cultures by defined factors" Cell, 2006; 126(4): 663-676.

Takahashi et al. "Induction of Pluripotent Stem Cells from Adult Human Fibroblasts by Defined Factors" Cell, 2007; 131: 861-872.

Upadhyay et al. "An analog of BIX-01294 selectively inhibits a family of histone H3 lysine 9 Jumonji demethylases" J Mol Biol., 2012; 416(3): 319-327.

Zhou et al. "Generation of induced pluripotent stem cells using recombinant proteins" Cell Stem Cell, 2009; 4(5): 381-384.

\* cited by examiner

| MCF (P2, day 4) | AP Staining |
|---|---|
| BIX I-1 | ++ |
| BIX I-2 | +++ |
| BIX I-3 | +++ |
| BIX I-4 | +++ |
| BIX I-5 | ++++ |
| BIX I-6 | ++ |
| BIX I-7 | + |
| BIX I-8 | + |
| BIX I-9 | + |
| BIX I-10 | ++ |
| BIX I-11 | ++++ |
| BIX I-12 | ++++ |
| BIX I-13 | + |
| BIX I-14 | + |
| BIX I-15 | + |
| BIX I-16 | +/- |
| BIX I-17 | +/- |
| BIX I-18 | + |
| BIX I-19 | + |
| BIX I-20 | - |
| BIX I-21 | + |

COMPOUNDS AND COMPOSITIONS USED TO EPIGENETICALLY TRANSFORM CELLS AND METHODS RELATED THERETO

CROSS REFERENCE TO RELATED APPLICATIONS

This application claims priority to U.S. Provisional Application No. 61/556,895 filed Nov. 8, 2011, hereby incorporated by reference in its entirety.

STATEMENT REGARDING FEDERALLY FUNDED RESEARCH

This invention was made with government support under Grant RC1GM092035 and UL1RR025008 awarded by the National Institutes of Health. The government has certain rights in the invention.

BACKGROUND

Naturally pluripotency occurs in early embryos and may be maintained in vitro in cultured Embryonic Stem (ES) cells harvested from blastocysts. Isolated ES cells can maintain their population by proliferating and self-renewing indefinitely and have the potential to differentiate into every lineage type in the body. Self-renewal allows ES cells in culture to undergo numerous cell cycles, including cell division, without losing pluripotency. Mouse ES cells require co-culture with a feeder layer of cells that provide essential factors. The culture medium typically contains leukemia inhibitory factor (LIF) for mouse ES cells, or fibroblast growth factors (FGFs) for human ES cells, to prevent differentiation. The aminopyrimidine, CHIR99021, is an inhibitor of glycogen synthase kinase 3β (GSK-3β). It enables the self-renewal of embryonic stem cells. Polychronopoulos et al., J Med Chem, 2004, 47: 935-946. Without feeders or cytokines, ES cells undergo spontaneous differentiation and lose their pluripotency.

Nuclear reprogramming, the process used to make induced pluripotent stem (iPS) cells, is the reverse of differentiation, in which differentiated cells revert to pluripotent cells. Induced generation of pluripotent stem cells from adult cells is an artificial manipulation that may not produce cells identical to naturally occurring pluripotent stem cells. However, some aspects of iPS cell generation may parallel the innate genetic processes that occur during embryonic development. Takahashi & Yamanaka, Cell, 2006, 126, 663-676, report a method for the generation of germline-competent induced pluripotent stem cells. See also Okita et al., Nature, 2007, 448, 313-317, 317. Pluripotent stem cells were induced from mouse fibroblasts by retroviral introduction of Oct3/4 (also called Pou5f1), Sox2, c-Myc and Klf4, and subsequent selection for Fbx15 (also called Fbxo15) expression. Huangfu et al., Nat Biotechnol, 2008, 26, 1269-1275, report the induction of pluripotent stem cells from primary human fibroblasts with only Oct4 and Sox2. However, the efficiency of these methods could be improved.

Several types of integrating viral vectors, including retrovirus and lentivirus have been used in iPS cell generation. Oncogenecity and heterogeneity are major concerns in virally induced human iPS cells because iPS derived offspring sometimes develop tumors. As an alternate approach, the protein products of the reprogramming genes have been delivered directly to cells, without viral DNA. Zhou et al., Cell Stem Cell, 2009, 4(5):381-4, report the use of recombinant proteins containing arginine residues at the C-terminus of each factor to reprogram cells with protein treatments plus the histone deacetylase (HDAC) inhibitor, valproic acid (VPA).

Epigenetic modifications are related to the reprogramming of somatic cells. In somatic cells, reprogramming factors are highly methylated in endogenous loci. However, Imamura et al., BMC Dev Biol, 2006, 6:34, report that these factors are hypomethylated in ES cells and iPS cells indicating that their promoters need to be demethylated in order to be reactivated and thereby reprogrammed to iPS cells. Doi et al., Nat Genet, 2009, 41:1350-1353 report that characterization of CpG methylation can help distinguish the identity of cell types such as fibroblasts, ES cells, and iPS cells.

Small molecules have been attempted to overcome these epigenetic blocks and enhance iPS cell generation. Huangfu et al., Nat Biotechnol, 2008, 26(7):795-7, report that the DNA methyltransferase inhibitor 5'-azacytidine increased the reprogramming efficiency. Shi et al., Cell Stem Cell, 2008, 2:525-528, report that a small-molecule inhibitor of G9a histone methyltransferase, BIX-01294, could enhance the induction of reprogramming in neural stem cells. Shi et al., Cell Stem Cell, 2008, 2(6)3:525-8568-574, report that administration of both BIX01294 and BayK8644, in combination with two factors (Oct4 and Klf4), is able to enhance the reprogramming efficiency of mouse neural progenitors and mouse embryonic fibroblasts. Krawetz & Rancourt, Bioessays, 2009, 31(3):336-43, report that Rho-associate kinase (ROCK) inhibitor, Y-27632, augments human iPS cell induction by enhancing cell survival. It has been reported that inhibitors of Wnt signaling, MEK, FGF, and TGF-β receptors also have effects on the generation and maintenance of ground-level pluripotency of iPS cells.

Shi et al., Cell Stem Cell, 2008, 2(6):525-8, report that BIX01294 and BayK8644, in combination with two factors (Oct4 and Klf4), enhanced the reprogramming efficiency of mouse neural progenitors and mouse embryonic fibroblasts. Upadyet et al., J Mol Biol, 2012, 416(3):319-27, report that an analog of BIX-01294 selectively inhibits a family of histone H3 lysine 9 Jumonji demethylases.

References cited herein are not an admission of prior art.

SUMMARY

This disclosure relates to compounds, compositions and methods of epigenetically transforming cells. In certain embodiments, the disclosure relates to methods of generating epigenetically altered cells comprising mixing isolated cells with compositions disclosed herein under conditions such that epigenetically altered cells are formed. In certain embodiments, the disclosure contemplates inducing cells, such as adult somatic cells or cells that are not naturally pluripotent, into cells with chemically induce pluripotency. In certain embodiments, the disclosure contemplates certain compounds disclosed herein, compounds disclosed herein optionally substituted with one or more substituents, derivatives, or salts thereof, for these purposes.

In certain embodiments, the disclosure contemplates methods comprising mixing cells with G9a methyltransferase inhibitors disclosed herein providing cells with stem cell-like properties and mixing these cells with a histone deacetylase inhibitor, such as valproic acid, to producing induced pluripotent cells. In certain embodiments, the methods further contemplate expansion of the induced pluripotent cells by mixing with other agents disclosed herein such as a ROCK inhibitor and/or a GSK-3beta inhibitor. In certain embodiments, the disclosure relates to compositions made by these methods, pharmaceutical compositions comprising these compositions, and therapeutic uses.

In certain embodiments, cell culture compositions comprise compounds disclosed herein or salts thereof typically in combination with one or more agents such as a DNA methylation inhibitor, a histone deacetylase (HDAC) inhibitor, a Rho-associated kinase (ROCK) inhibitor, Wnt inhibitor, GSK-3beta inhibitor, and/or a dihydropyridine. In certain embodiments, the DNA methylation inhibitor is 5-azacitidine or decitabine. In certain embodiments, the HDAC inhibitor is vorinostat-suberoylanilide hydroxamic acid (SAHA), trichostatin A (TSA), sodium butyrate, and/or valproic acid (VPA). In certain embodiments, the ROCK inhibitor is 4-(1-aminoethyl)-N-(pyridin-4-yl)cyclohexanecarboxamide (Y-27632) or salt thereof. In certain embodiments, the dihydropyridine is 1,4-dihydro-2,6-dimethyl-5-nitro-4-[2-(trifluoromethyl)phenyl]-3-pyridinecarboxylic acid, methyl ester (BayK8644), ester, derivative, or salt thereof. In certain embodiments, the GSK-3beta inhibitor is 6-[[2-[[4-(2,4-dichlorophenyl)-5-(5-methyl-1H-imidazol-2-yl)-2 pyrimidinyl]amino]ethyl]amino]-3-pyridinecarbonitrile (CHIR99201) or salt thereof. The composition may also contain one or more of the following compounds fibroblast growth factor receptor inhibitor N-[2-[[4-(diethylamino)butyl]amino]-6-(3,5-dimethoxyphenyl)pyrido[2,3-d]pyrimidin-7-yl]-N'-(1,1-dimethylethyl)urea (PD173074) and/or inhibitor of TGF-β type I receptor, 3-(6-methyl-2-pyridinyl)-N-phenyl-4-(4-quinolinyl)-1H-pyrazole-1-carbothioamide (A-83-01) and/or 4-[4-(1,3-benzodioxol-5-yl)-5-(2-pyridinyl)-1H-imidazol-2-yl]benzamide (SB 431542) and/or DNA methyltransferase inhibitor N-phthalyl-L-tryptophan (RG 108).

In certain embodiments, the cell culture composition may comprise leukemia inhibitory factor (LIF), fibroblast growth factors (FGFs), MEK, or TGF-β. In certain embodiments, the cell culture composition may comprise one or more factors selected from OCT4, SOX2, KLF4, c-MYC, L-MYC, NANOG, LIN28, JMJD1a, and JMJD2c.

In certain embodiments, the disclosure relates to methods of generating chemically induced pluripotent stem cells comprising mixing isolated somatic cells with a composition with compound disclosed herein under conditions such that cells with induced epigenetic changes are produced such as in the case where induced pluripotent stem cells are formed. Typically, the induced pluripotent stem cells have elevated levels of membrane alkaline phosphatase (AP), express elevated levels of one or more, two or more or all of OCT4 and NANOG, SSEA-3, SSEA-4, TRA-1-60, and TRA-1-8, and express elevated mRNA of one or more of the genes selected from Pou5f1, Nanog, Sox2, Klf4, Eras, Fgf4, Tdgf1, NrOb1, Zfp296, Zfp42, Ecat1, Fbxo15, Dppa5a, Gdf3, and Slc2a3.

In certain embodiments, isolated cells are somatic cells, human peripheral blood cells, fibroblasts, keratinocytes, hepatocytes, bone marrow mononuclear cells, amniotic fluid and yolk-sac cells, adipose-derived stem cells, T-lymphocytes, B-lymphocytes, neural progenitor cells, pancreatic beta cells, melanocytes, liver epithelial cells, cord blood cells, dermal papilla cells, urothelial, or mesenchylmal stromal cells.

In certain embodiments, the disclosure relates to compositions comprising induced pluripotent stem cells made by the methods disclosed herein.

It is object of certain embodiments of the disclosure to produce human iPS cells useful for generation of disease-specific iPS cells or patient-specific iPS cells for autologous cell therapy. Another object of certain embodiments of the disclosure is to reprogram human blood cells by inducing the expression of endogenous iPS factor genes with epigenetic regulators such as certain compounds disclosed herein. Another object of certain embodiments of the disclosure is to generate iPS cells by modulating the epigenetic status of pluripotency genes by certain compounds without using genetic material. In certain embodiments, isolated somatic cells are obtained from human peripheral blood (PB).

In certain embodiments, the disclosure relates to methods of treating diseases or conditions by administering or implanting effective amounts of induced pluripotent stem cell compositions disclosed herein to a subject in need thereof. Contemplated embodiments include the treatment or prevention of heart disease, diabetes, coronary artery disease, neurodegenerative disease such as Parkinson's and Alzheimer's disease, musculoskeletal disorders, spinal cord injury, stroke, autoimmune diseases, and major trauma. In certain embodiments, cell based therapies are contemplated such as bone marrow cell transplantation which are used to treat leukemia, aplastic anemia, and immune deficiency diseases.

In some embodiments, it is contemplated that compositions disclosed herein can be administered to subject before, during or after certain medical procedures, such as, organ transplants (heart, kidneys, liver, lungs, pancreas, intestine, and thymus) or other surgeries that reduce blood flow (cardiovascular surgery).

In some embodiments, it is contemplated that compounds disclosed herein can be used in biological (organ, tissue, or cell) storage, culture mediums or cryopreservation, typically aqueous or DMSO or mixed solutions maintained at or below room temperatures, which may contain other ingredients such as, but not limited to, salts (sodium chloride, sodium lactate, calcium chloride, potassium chloride), amino acids, saccharides or polysaccharides (glucose, dextran, chondroitin, hydroxyethyl starch), vitamins (thiamine, ascorbic acid, calciferol, riboflavin, pyridoxine, tocopherol, cobalamins, phylloquinone, pantothenic acid, biotin, niacin, folic acid) and/or adenosine triphosphate or precursors (adenosine, inosine, and adenine). Other contemplated components include bovine serum albumin, human recombinant bFGF and TGFβ, pipecolic acid, and GABA.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

DETAILED DESCRIPTION

Figure 1:
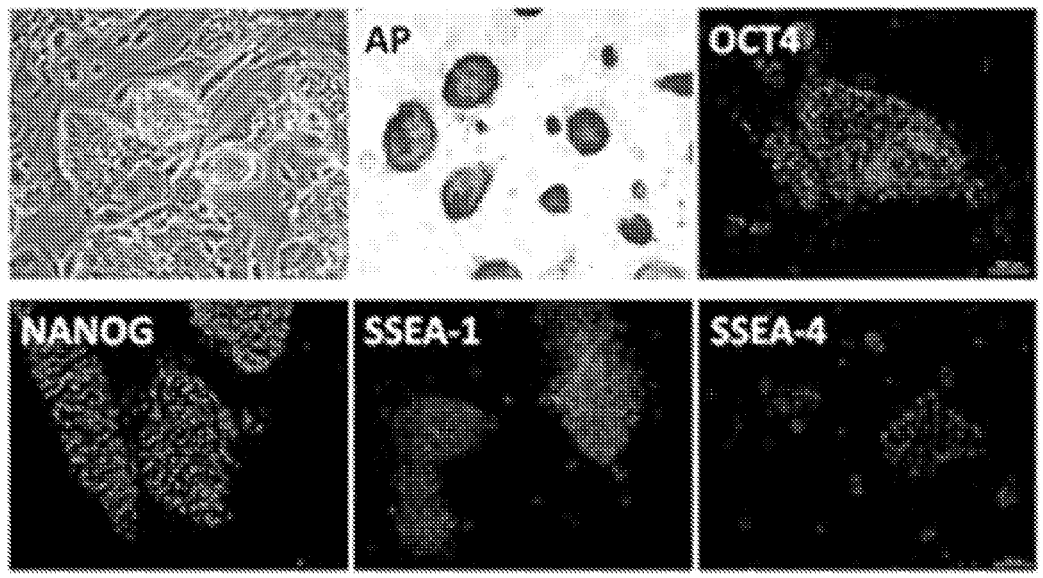
FIG. 1 illustrates ES cell-like colony morphology and gene expression pattern of ChemiPS. ChemiPS cells were stained with substrates of alkaline phosphatase (AP), and with antibodies against to mouse POU5F1, SSEA-1, and SSEA-4 visualized by Cy3-conjugated secondary antibody. The colonies of ChemiPS cells exhibit strong positive signals for AP, POU5F1, and SSEA-1, but negative signals for SSEA-4, showing the typical characteristics of mouse ES cells.
Figure 2:
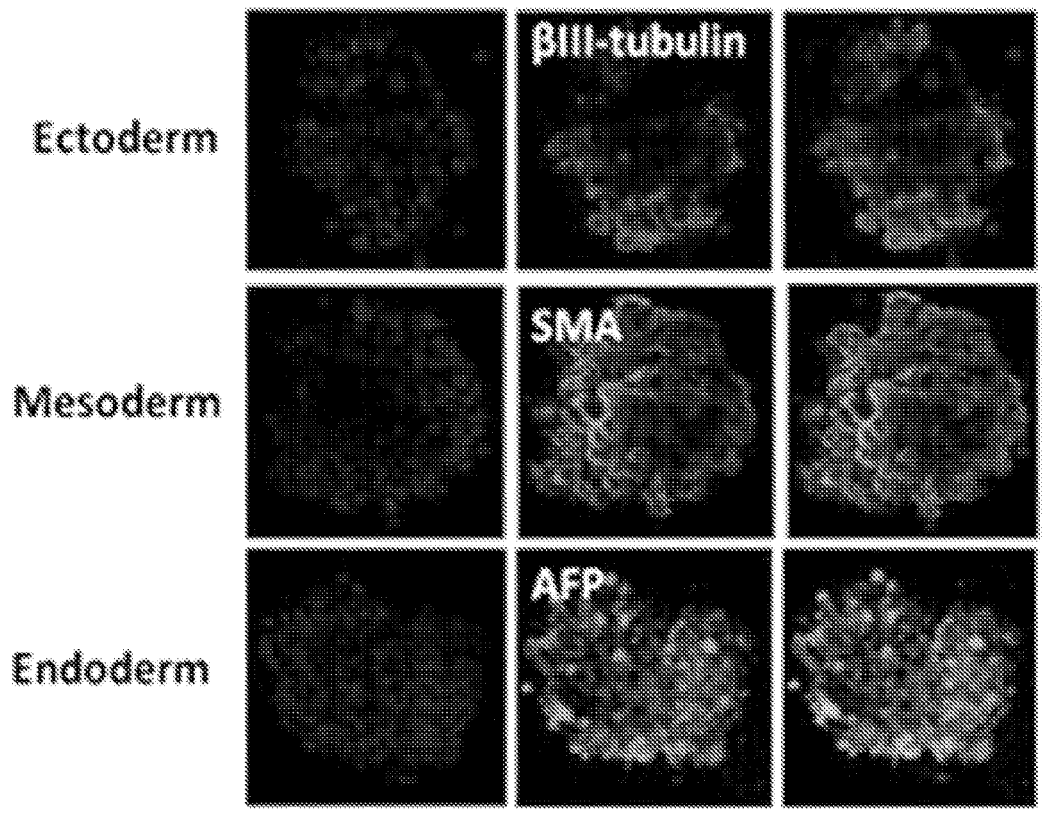
FIG. 2 illustrates the expression of three germ layer specific makers during EB formation of ChemiPS. ChemiPS cells form embryoid bodies (EBs) in suspension culture after 9 days. Immunocytochemistry of differentiated cells in these EBs showed expression of markers for ectoderm (βIII-tubulin), mesoderm (SMA), and endoderm (AFP).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Prior to describing the various embodiments, the following definitions are provided and should be used unless otherwise indicated.

As used herein, the term "induced pluripotent stem cells" refers to cells induced to a state that can differentiate into at least one cell of the endoderm, mesoderm and ectoderm. Such characteristics include the expression of certain genes and proteins, chromatic methylation patterns, doubling time, embryoid body formation, teratoma formation, and differentiability. Induced pluripotent stem cells typically express alkaline phosphatase, Oct 4, Sox2, Nanog, and other pluripotency-promoting factors. It is not intended that the cells be entirely identical to embryonic cells. Induced pluripotent stem cells may not necessarily be capable of differentiating into any type of cell. SSEA-1 is a mouse ESC/iPSC specific marker; SSEA-3 and -4 are not expressed in mouse ESC/iPSC. However, human ESC/iPSC express SSEA-3 and SSEA-4, not SSEA-1. SSEA-1 is mouse iPSC specific. SSEA-3, SSEA-4 is human iPSC specific. TRA-1-60 and TRA-1-8 are usually used to identify human PSC.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above attached through a sulfur bridge. An example of an alkylthio is methylthio, (i.e., —S—CH$_3$).

"Alkoxy" refers to an alkyl group as defined above attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above attached through an amino bridge. An example of an alkylamino is methylamino, (i.e., —NH—CH$_3$).

"Alkanoyl" refers to an alkyl as defined above attached through a carbonyl bride (i.e., —(C=O)alkyl).

"Alkylsulfonyl" refers to an alkyl as defined above attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfinyl" refers to an alkyl as defined above attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO$_2$R$_b$, —C(=O)R$_a$, —C(=O)OR$_a$, —C(=O)NR$_a$R$_b$, —OC(=O)NR$_a$R$_b$, —OR$_a$, —SR$_a$, —SOR$_a$, —S(=O)$_2$R$_a$, —OS(=O)$_2$R$_a$ and —S(=O)$_2$OR$_a$. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, rodent, monkey or domestic pet.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing an oxygen atom with a sulfur or nitrogen atom or replacing an amino group with a hydroxyl group or vice versa. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

As used herein, the term "combination with" when used to describe administration with an additional treatment means that the agent may be administered prior to, together with, or after the additional treatment, or a combination thereof.

Compounds

In certain embodiments, the disclosure contemplates the use of compounds disclosed herein to generate induced pluripotent stem cells. Although it is not intended that certain embodiments of the disclosure be limited by any particular mechanism, it is believed that the compounds typically have the ability to inhibit the function of methyltransferases such as G9a methyltransferase.

In certain embodiments, contemplated compounds have Formula I:

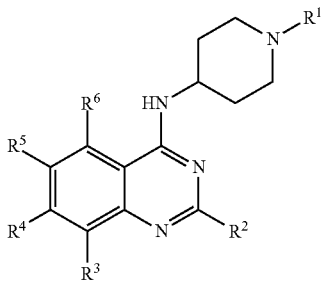

Formula I or salts thereof wherein, $R^1$, $R^2$, $R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^8$; and $R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^4$ is alkoxy optionally substituted with one or more, the same or different, $R^7$.

In certain embodiments, $R^2$ is alkylamino optionally substituted with one or more, the same or different, $R^7$.

In certain embodiments, $R^2$ is a heterocyclyl optionally substituted with one or more, the same or different, $R^7$.

In certain embodiments, $R^1$ is alkyl or benzyl optionally substituted with one or more, the same or different, $R^7$.

In certain embodiments, contemplated compounds have Formula IA:

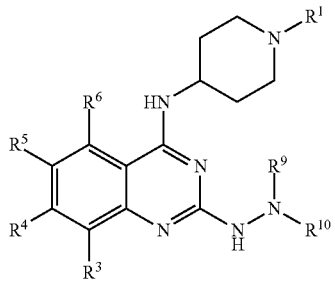

Formula IA or salts thereof wherein, $R^1$, $R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^8$;

$R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^9$ and $R^{10}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^9$ and $R^{10}$ are optionally substituted with one or more, the same or different, $R^{11}$;

or $R^9$ and $R^{10}$ come together to form a heterocyclyl optionally substituted with one or more, the same or different, $R^{11}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$ is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, contemplated compounds are selected from:
N-(1-benzylpiperidin-4-yl)-2-(4-methylpiperazin-1-yl)quinazolin-4-amine,
N-(1-benzylpiperidin-4-yl)-2-(4-methyl-1,4-diazepan-1-yl)quinazolin-4-amine,
N-(1-benzylpiperidin-4-yl)-6,7-dimethoxy-2-(4-methyl-1,4-diazepan-1-yl)quinazolin-4-amine,
N-(1-benzylpiperidin-4-yl)-6,7-dimethoxy-2-(4-methylpiperazin-1-yl)quinazolin-4-amine,
N-(1-benzylpiperidin-4-yl)-6,7-dimethoxy-2-morpholinoquinazolin-4-amine,
N-(1-benzylpiperidin-4-yl)-2-morpholinoquinazolin-4-amine,
N-(1-benzylpiperidin-4-yl)-2-thiomorpholinoquinazolin-4-amine, N-(1-benzylpiperidin-4-yl)-2-(piperidin-1-yl)quinazolin-4-amine,
2-(azepan-1-yl)-N-(1-benzylpiperidin-4-yl)quinazolin-4-amine,
N-(1-benzylpiperidin-4-yl)-2-(4-methylpiperidin-1-yl)quinazolin-4-amine,
$N^4$-(1-benzylpiperidin-4-yl)-$N^2$-(piperidin-1-yl)quinazoline-2,4-diamine,
N-(1-benzylpiperidin-4-yl)-2-(pyrrolidin-1-yl)quinazolin-4-amine,
N-(1-benzylpiperidin-4-yl)-2-(4-(pyridin-2-yl)piperazin-1-yl)quinazolin-4-amine,
(4-(4-((1-benzylpiperidin-4-yl)amino)quinazolin-2-yl)piperazin-1-yl)(phenyl)methanone,
$N^4$-(1-benzylpiperidin-4-yl)-$N^2$-(3-(dimethylamino)propyl)quinazoline-2,4-diamine,
2-((4-((1-benzylpiperidin-4-yl)amino)quinazolin-2-yl)amino)ethanol,
$N^4$-(1-benzylpiperidin-4-yl)-$N^2$-(4-methylpiperazin-1-yl)quinazoline-2,4-diamine,
$N^4$-(1-benzylpiperidin-4-yl)-$N^2$-morpholinoquinazoline-2,4-diamine,
N-(1-benzylpiperidin-4-yl)-2-(2-methylpiperidin-1-yl)quinazolin-4-amine,
7-((5-aminopentypoxy)-$N^4$-(1-benzylpiperidin-4-yl)-$N^2$-(3-(dimethylamino)propyl)-6-methoxyquinazoline-2,4-diamine,
N-(1-benzylpiperidin-4-yl)-2-(4-phenylpiperazin-1-yl)quinazolin-4-amine, and
7-((5-aminopentypoxy)-$N^4$-(1-(5-aminopentyl)piperidin-4-yl)-$N^2$-(3-(dimethylamino)propyl)-6-methoxyquinazoline-2,4-diamine or salts thereof.

In certain embodiments, contemplated compounds have Formula II:

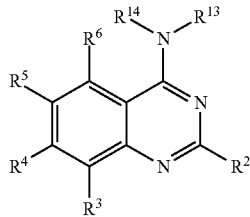

Formula II or salts thereof wherein, $R^2$, $R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^2$, $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^7$ is optionally substituted with one or more, the same or different, $R^8$;

$R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{13}$ and $R^{14}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^{13}$ and $R^{14}$ are optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^{13}$ and $R^{14}$ are hydrogen or alkyl optionally substituted with one or more, the same or different, $R^{15}$.

In certain embodiments, $R^4$ is alkoxy optionally substituted with one or more, the same or different, $R^7$.

In certain embodiments, $R^2$ is alkylamino optionally substituted with one or more, the same or different, $R^7$.

In certain embodiments, $R^2$ is a alkyl or heterocyclyl optionally substituted with one or more, the same or different, $R^7$.

In certain embodiments, contemplated compounds are selected from:
7-((5-aminopentypoxy)-$N^2$-(3-(dimethylamino)propyl)-6-methoxy-$N^4$,$N^4$-dimethylquinazoline-2,4-diamine and
7-((5-aminopentypoxy)-6-methoxy-$N^2$,$N^2$,$N^4$,$N^4$-tetramethylquinazoline-2,4-diamine or salts thereof.

Epigenetic Regulation of Induced Pluripotency

Gene expression is affected by chromatin. Chromatin is the complex of DNA and the histone proteins. Chromatin remodeling occurs through post translational modification of the histone proteins. Chromatic remodeling may also occur with the addition of methyl groups to the DNA. Cytosines are often converted to 5-methylcytosine in CG sequences of DNA, often referred to as methylated "CpGs." 5-Methylcytosine, like cytosine, pairs with guanine Highly methylated DNA tends to be less transcriptionally active. Histone acetylation, methylation, ubiquitylation, and phosphorylation modifications typically occur at the N-termini of histones. For example, acetylation of the K14 and K9 lysines of the tail of histone H3 by histone acetyltransferase enzymes (HATs) has typically been correlated with transcriptional competence. Methylation of lysine 9 of histone H3 has typically been associated with constitutively transcriptionally silent chromatin.

Evidence suggests that epigenetic regulation, that is, alterations in post-translational modifications of histones and post-replicational DNA methylation at CpG sequences, underlie the simultaneous activation of pluripotency-associated genes and repression of differentiation-specific genes necessary to achieve the reprogramming of somatic cells to pluripotent cells.

Although it is not intended that embodiments of the disclosure be limited by any particular mechanism, it is believed that the follow occurs during reprogramming to induced pluripotent stem cells. The four endogenous reprogramming factors (OCT4, SOX2, KLF4, c-MYC) typically lose CpG methylation at their promoters and become activated compared to somatic cells. Histones at promoters of Oct4, Nanog and Sox2 are highly methylated at H3 lysine 4 (H3K4), a marker for active transcription, and are devoid of methylation at H3K9 and H3K27, which are both markers for transcription repression in ES cells. Jmjd1a and Jmjd2c are histone H3K9 demethylases important for self-renewal of ES cells. Oct4 positively regulates the expression of Jmjd1a and Jmjd2c, and Jmjd2c activates Nanog expression by demethylating H3K9 at the Nanog promoter.

Upon differentiation of embryonic cells, Oct4 becomes silenced in conjunction with hypermethylation of H3K9 by the G9a histone methyltransferase and subsequently forms heterochromatin. G9a and G9a-like protein (GLP) are euchromatin-associated methyltransferases that repress transcription by mono- and di-methylation of histone H3 at lysine 9 (H3K9me1 and H3K9me2). H3K9me1 and H3K9me2 are silencing marks that are lost when tumor suppressor genes are reactivated following treatment with 5-aza-2'-deoxycytidine (5-aza), which is an FDA approved inhibitor of DNA methylation. Thus, the enzymes that catalyze the formation of H3K9me1 and me2 are appealing targets to induce dynamic changes during reprogramming.

The status of histone methylation on the promoter of specific genes, for example the pluripotency-determining gene Oct3/4, is mediated by the histone methyltransferase G9a. The efficiency of iPS cell generation was greatly enhanced by the treatment of inhibitor of G9a methyltransferase with limited defined factors. Also, the inhibitors of histone deacetylase and DNA methylation, which regulate the acetylation status of histone protein and methylation status of DNA for gene silencing, highly increased the efficiency of generation of iPS cells. Certain compounds disclosed herein can modulate reprogramming and maintain self-renewal to induce pluripotency in somatic cells without any genetic factors. Chemically induced pluripotent stem (ChemiPS) cells typically have no genetic modifications; therefore, these cells may be used as sources of cell-based therapeutics in safer way to treat patients with incurable diseases.

Generating iPS cells from peripheral blood (PB) of healthy volunteers and coronary artery disease (CAD) patients is contemplated herein. PB is obtainable in a non-surgical and aseptic manner.

EXAMPLES

Synthesis of Quinazoline Derivatives

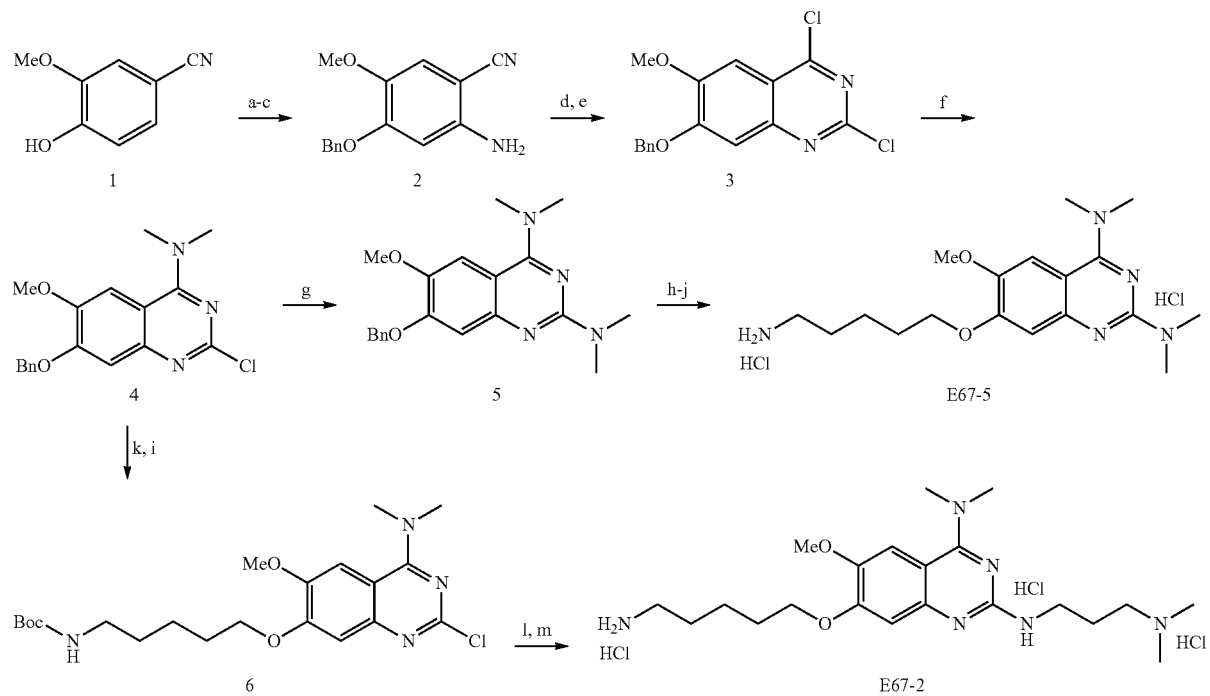

Reagents and conditions: (a) Benzyl bromide, $K_2CO_3$, dry DMF, rt; (b) $HNO_3$ 69.5%, $(Ac)_2O$, 0° C. then rt; (c) iron dust, $NH_4Cl$, i-PrOH—$H_2O$ (5:3), reflux; (d)i) methyl chloroformate, DIPEA, DMF-DCM (2:1), 0° C. then rt, ii) $H_2O_2$ 30%, NaOH, EtOH; (e) $POCl_3$, N,N-diethylaniline, reflux; (f)dimethylamine 2M in THF, dry THF, rt; (g) dimethylamine 2M in THF, dry THF, 110° C., sealed tube; (h) $H_2$, Pd—C, dry THF-MeOH (2:1), 1 atm, rt; (i) tert-butyl (5-hydroxypentyl)carbamate, $PPh_3$, DIAD, dry THF, $N_2$, rt; (j) HCl 4N in dioxane, dry THF, rt; (k) TFA, reflux; (l) $N^1,N^1$-dimethylpropane-1,3-diamine, 110° C., sealed tube; (m) HCl 4N in dioxane, dry THF-MeOH (1:1), rt.

7-((5-aminopentypoxy)-$N^2$-(3-(dimethylamino)propyl)-6-methoxy-$N^4,N^4$-dimethylquinazoline-2,4-diamine (E67-

2): $^1$H-NMR (400 MHz, DMSO) δ 1.50 (m, 2H, CH$_2$CH$_2$CH$_2$O), 1.65 (m, 2H, CH$_2$CH$_2$CH$_2$O), 1.81 (m, 2H, CH$_2$CH$_2$O), 2.80 (m, 2H, H$_3$N$^+$CH$_2$CH$_2$), 3.26 (s, 6H, N(CH$_3$)$_2$), 3.45 (s, 6H, N(CH$_3$)$_2$), 3.87 (s, 3H, OCH$_3$), 4.08 (m, 2H, CH$_2$CH$_2$CH$_2$O), 7.45 (s, 1H, H quinazoline ring), 7.76 (s, 1H, H quinazoline ring), 7.99 (s br, 3H, H$_3$N$^+$), 12.1 (s br, 1H, HN$^-$ quinazoline ring).

7-((5-aminopentypoxy)-6-methoxy-N$^2$,N$^2$,N$^4$,N$^4$-tetramethylquinazoline-2,4-diamine (E67-5): $^1$H-NMR (400 MHz, DMSO) δ 1.50 (m, 2H, CH$_2$CH$_2$CH$_2$O), 1.64 (m, 2H, CH$_2$CH$_2$CH$_2$CH$_2$O), 1.81 (m, 2H, CH$_2$CH$_2$O), 1.99 (m, 2H, NHCH$_2$CH$_2$), 2.74 (s, 6H, $^+$HN(CH$_3$)$_2$), 2.80 (m, 2H, H$_3$N$^+$CH$_2$CH$_2$), 3.11 (m, 2H, CH$_2$CH$_2$N(CH$_3$)$_2$H$^+$), 3.47 (s, 6H, N(CH$_3$)$_2$), 3.49 (m, 2H, NHCH$_2$CH$_2$CH$_2$), 3.86 (s, 3H, OCH$_3$), 4.09 (m, 2H, CH$_2$CH$_2$CH$_2$O), 7.15 (s, br, 1H NHCH$_2$CH$_2$CH$_2$), 7.45 (s, 1H, H quinazoline ring), 7.93 (m, 4H, H quinazoline ring and H$_3$N$^+$), 10.6 (s, br, $^+$HN(CH$_3$)$_2$), 12.8 (s br, 1H, HN$^+$ quinazoline ring).

Additional compound below were prepared by using the same or similar conditions by substituting appropriate starting materials.

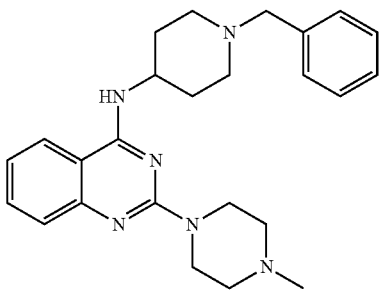

N-(1-benzlpiperidin-4-yl)-2-(4-methylpiperazin-1-yl)quinazolin-4-amine

I-1

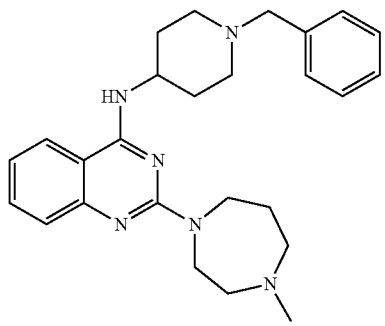

N-(1-benzylpiperidin-4-yl)-2-(4-methyl-1,4-diazepan-1-yl)quinazolin-4-amine

I-2

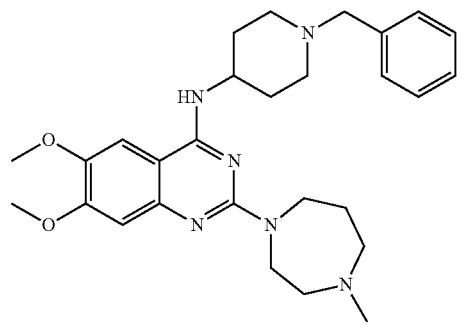

N-(1-benzylpiperidin-4-yl)-6,7-dimethoxy-2-(4-methyl-1,4-diazepan-1-yl)quinazolin-4-amine (BIX-01294)

I-3

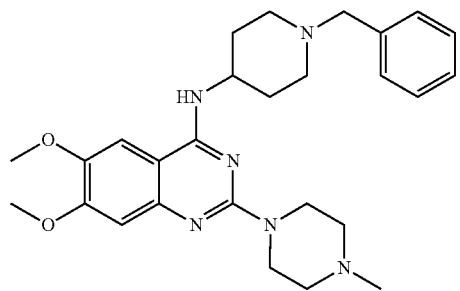

N-(1-benzylpiperidin-4-yl)-6,7-dimethoxy-2-(4-methylpiperazin-1-yl)quinazolin-4-amine

I-4

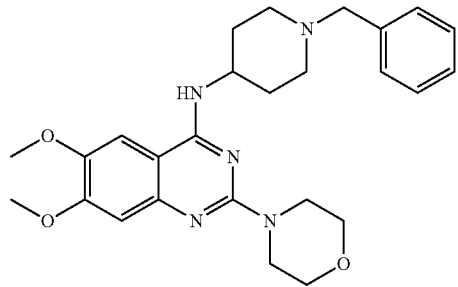

N-(1-benzylpiperidin-4-yl)-6,7-dimethoxy-2-morpholinoquinazolin-4-amine

I-5

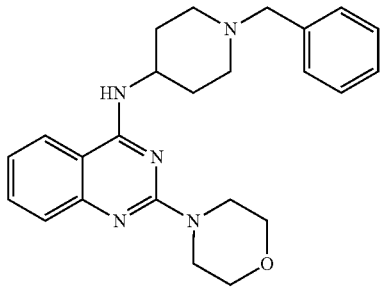

N-(1-benzylpiperidin-4-yl)-2-morpholinoquinazolin-4-amine

I-6

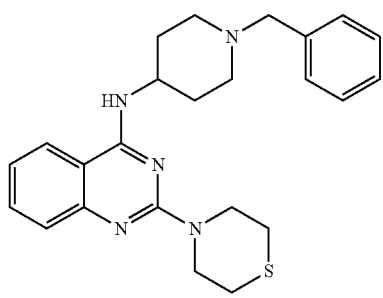

N-(1-benzylpiperidin-4-yl)-2-thiomorpholinoquinazolin-4-amine

I-7

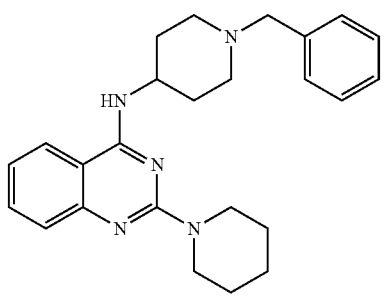

N-(1-benzylpiperidin-4-yl)-2-(piperidin-1-yl)quinazolin-4-amine

I-8

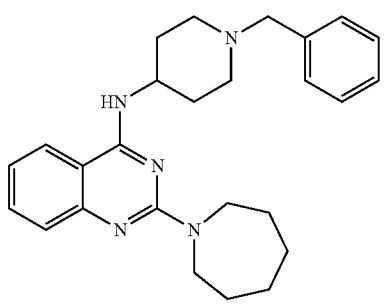

2-(azepan-1-yl)-N-(1-benzylpiperidin-4-yl)quinazolin-4-amine

I-9

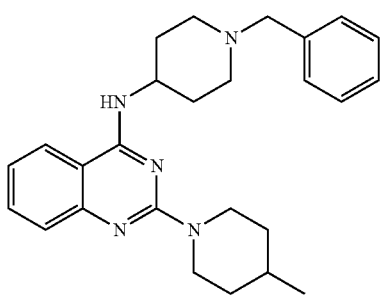

N-(1-benzylpiperidin-4-yl)-2-(4-methylpiperidin-1-yl)quinazolin-4-amine

I-10

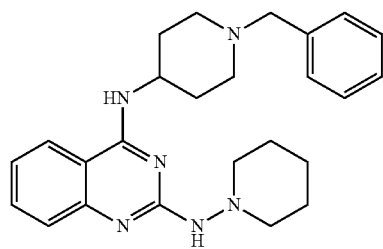

$N^4$-(1-benzylpiperidin-4-yl)-$N^2$-(piperidin-1-yl)quinazoline-2,4-diamine

I-11

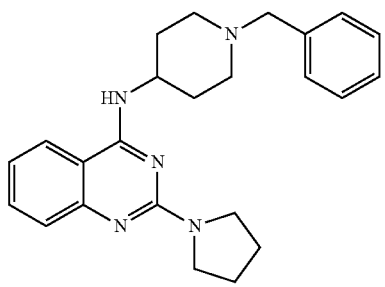

N-(1-benzylpiperidin-4-yl)-2-(pyrrolidin-1-yl)quinazolin-4-amine

I-12

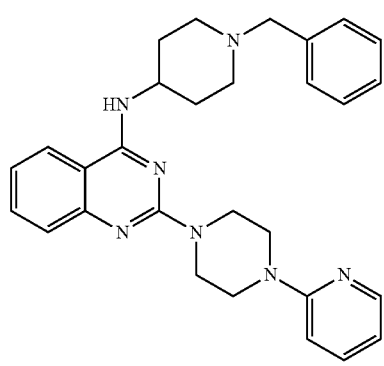

N-(1-benzylpiperidin-4-yl)-2-(4-(pyridin-2-yl)piperazin-1-yl)quinazolin-4-amine

I-13

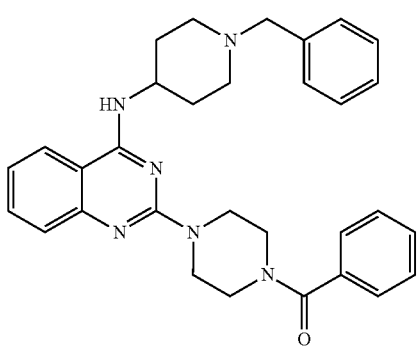

(4(4-((1-benzylpiperidin-4-yl)amino)quinazolin-2-yl)piperazin-1-yl)(phenyl)methanone

I-14

-continued

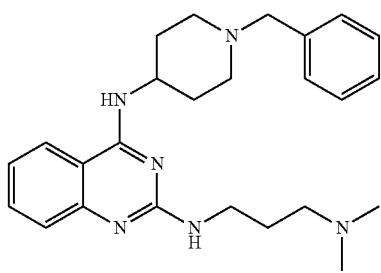

$N^4$-(1-benzylpiperidin-4-yl)-$N^2$-(3-(dimethylamino)propyl)quinazoline-2,4-diamine

I-15

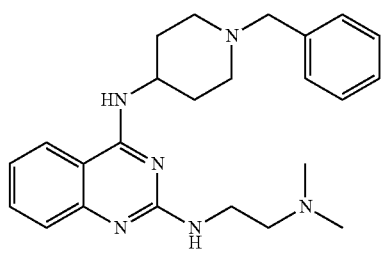

$N^4$-(1-benzylpiperidin-4-yl)-$N^2$-(2-(dimethylamino)ethyl)quinazoline-2,4-diamine

I-16

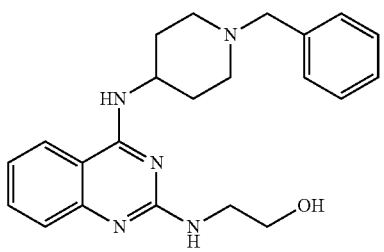

2-((4-((1-benzylpiperidin-4-yl)amino)quinazolin-2-yl)amino)ethanol

I-17

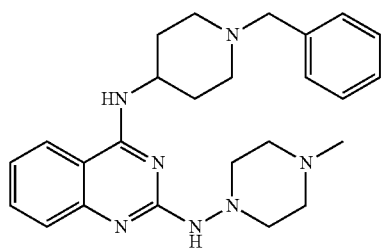

$N^4$-(1-benzylpiperidin-4-yl)-$N^2$-(4-methylpiperazin-1-yl)quinazoline-2,4-diamine

I-18

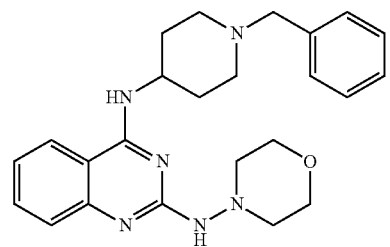

$N^4$-(1-benzylpiperidin-4-yl)-$N^2$-morpholinoquinazoline-2,4-diamine

I-19

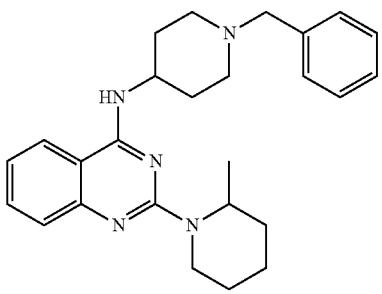

N-(1-benzylpiperidin-4-yl)-2-(2-methylpiperidin-1-yl)quinazolin-4-amine

I-20

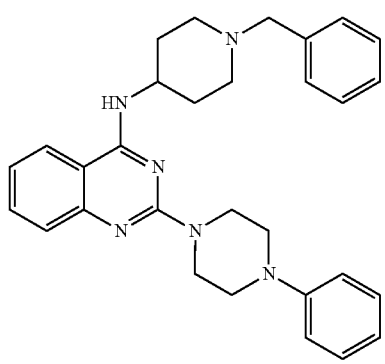

N-(1-benzylpiperidin-4-yl)-2-(4-phenylpiperazin-1-yl)quinazolin-4-amine

I-21

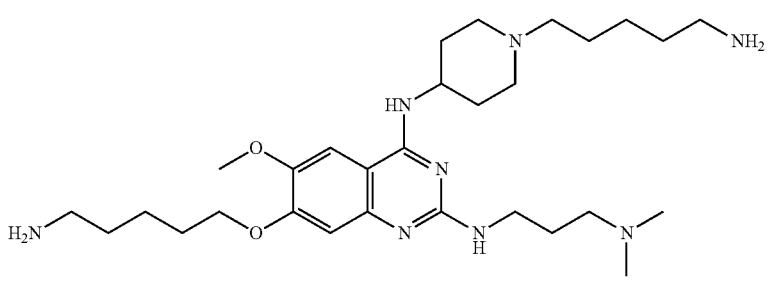

7-((5-aminopentyl)oxy)-N$^4$-(1-(5-aminopentyl)piperidin-4-yl)-N$^2$-(3-(dimethylamino)propyl)-6-methoxyquinazoline-2,4-diamine

E72

Generation of Chemically Induced Pluripotent Stem Cells with G9a and GLP Inhibitors:

To generate iPS cells, quinazoline derivatives were administered to culture media of primary mouse cardiac fibroblasts for 10 days, which were isolated and cultured from mouse embryo adult heart or skin. At 11 days post-treatment, cell clumps showing ES cell-like morphology were selected and transferred to feeder STO cells (mouse embryonic fibroblast cell line) for expansion. At the point of transferring to feeder cells, Rho-associated kinase (ROCK) inhibitor, Y-27632, and glycogen synthase kinase-3 beta (GSK-3β) inhibitor, CHIR99021 were treated for 2 days with new culture media change to increase cell survival by modulating Wnt signal pathway. The mouse leukemia inhibitory factor (LIF) was added to cell culture media after transferring to STO cells for the maintenance of self-renewal of potential ES-like cells.

Figure 3:
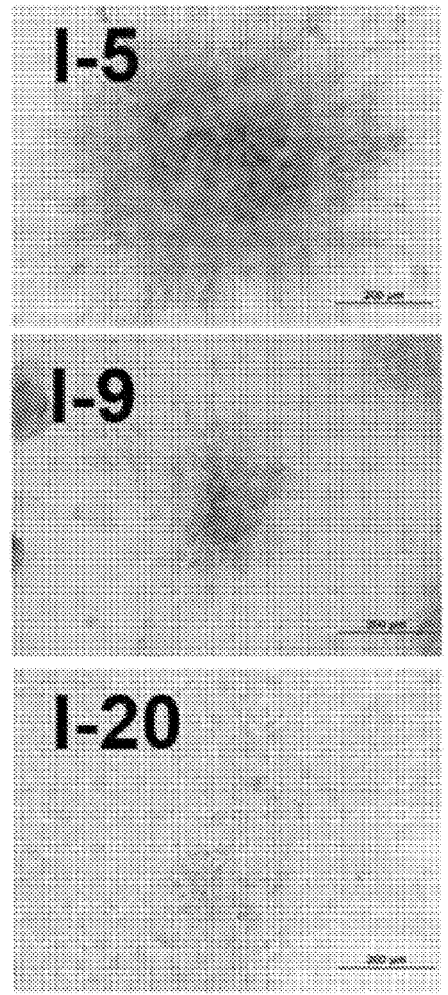
FIG. 3 shows data on the alkaline phosphatase expression patterns of cells treated with compounds disclosed herein. (Left table) The intensity of AP staining is indicated by positive (+) and negative (−). (Right panel) Cells were stained with AP substrates.

Colonies displaying ES cell-like morphology were propagated manually or treated with trypsin, and expanded for the subsequent experiments. Typically, a successful generation of iPS cells can be initially judged by presence of tightly packed and flat colonies composing cells characterized by large nuclei and scant cytoplasm. After 10 to 11 passages, colonies of cells were stained with alkaline phosphatase (AP) substrates to determine which G9a inhibitors were able to induce pluripotency. Certain analogues were more potent for generating highly AP-positive cells (FIG. 3).

Figure 4A:
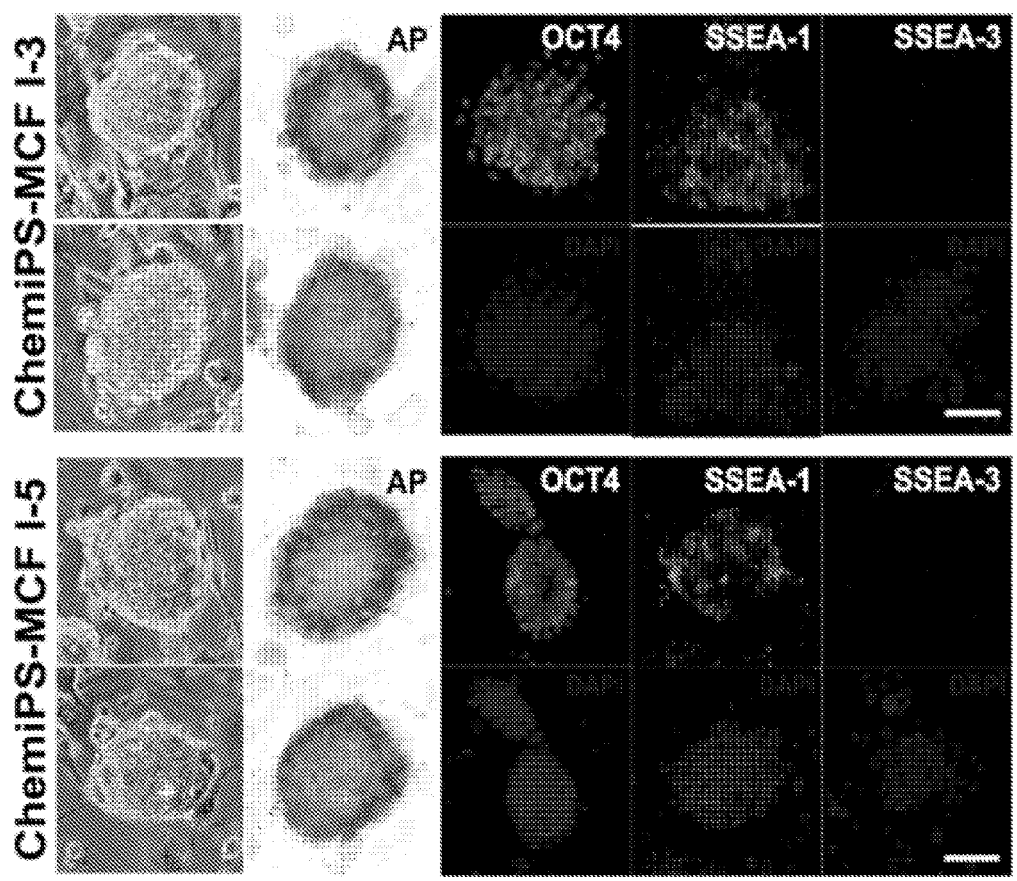
FIGS. 4A-B show data on expression of pluripotency genes in iPS cells. A.ChemiPS-MCF I-3 and -I-5 cells showed ES cell-like morphology, positivity for AP, and stained positive for Oct4, SSEA-1, and SSEA-3. B.RT-PCR analysis. ES cell marker genes were expressed in ChemiPS cells and mouse ES cells (D3) but not cardiac fibroblasts. Eif4g2 and Gapdh were used as controls.
Figure 4B:
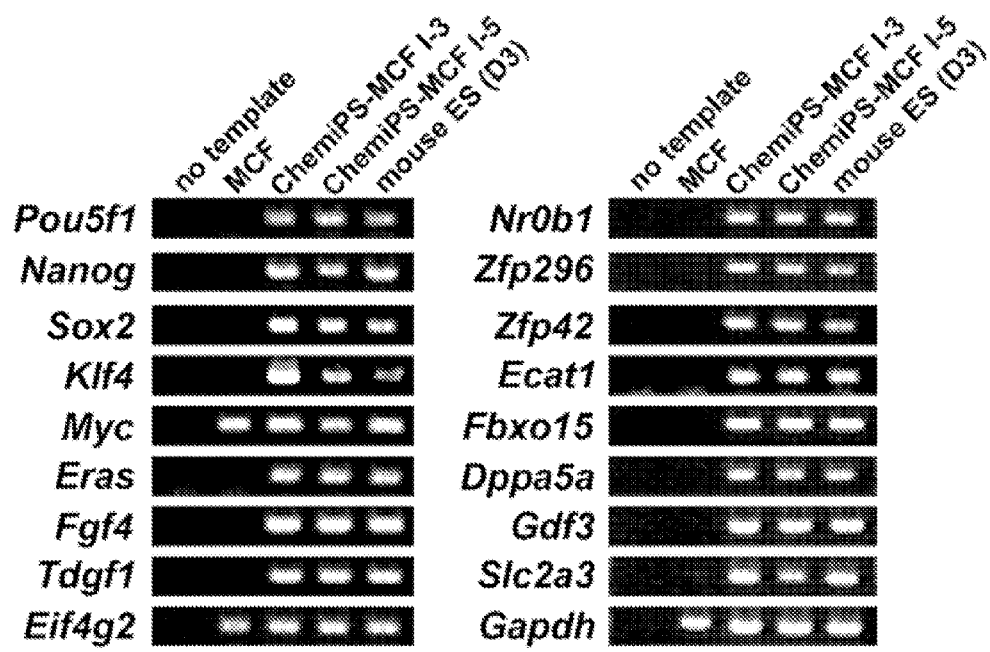

Cell lines that showed heightened expression levels of AP signal as a marker of pluripotency were selected for the further verification. To verify whether the chemical induced pluripotent stem (chemiPS) cells display characteristics of mouse ES cells, immunohistochemistry was performed with antibodies against OCT4, SSEA-1 as markers of pluripotency, and SSEA-4 as a negative pluripotency marker for mouse ES cells. Putative chemiPS cells showed stronger signals for AP, OCT4, and SSEA-1 with ES-cell like morphology. ChemiPS-MCF I-3 and ChemiPS-MCF I-5 exhibited strong signals for AP, OCT4, SSEA-1, and SSEA-4 with ES-cell like morphology (FIG. 4A). RT-PCR showed that ES cell marker genes (PouSf1, Nanog, Sox2, Klf4, Eras, Fgf4, Tdgf1, Nr0b1, Zfp296, Zfp42, Ecat1, Fbxo15, Dppa5a, Gdf3, and S1c2a3) were all expressed similar to mouse ES cells (D3 line), but not like somatic cells (MCF) (FIG. 4B).

Figure 5A:
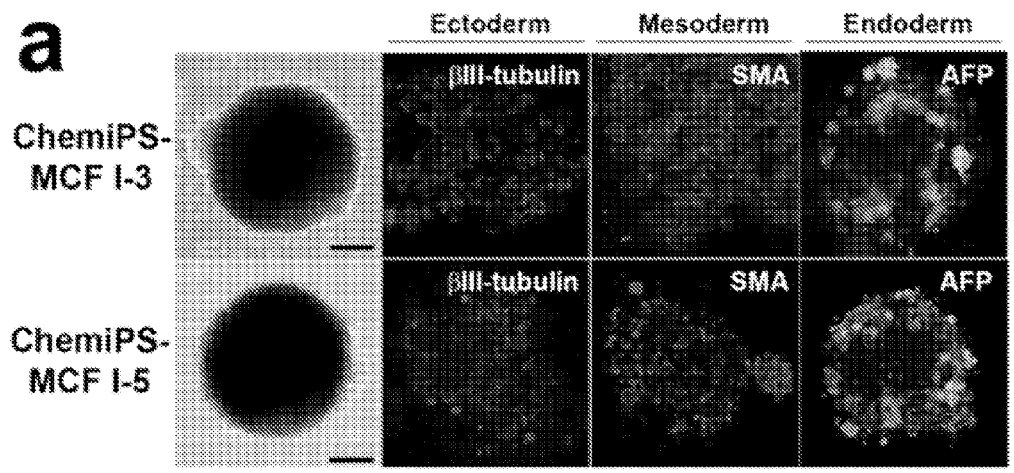
FIGS. 5A-C show data on multi-lineage differentiation capacity of ChemiPS. a. ChemiPS cells form EBs in suspension culture after 9 days. Different cell types were stained to show the expression markers for ectoderm (βIII-tubulin), mesoderm (SMA), and endoderm (AFP) with whole EBs in suspension culture. Scale bar, 100 µm. b.qRT-PCR results showing gene expression from three germ layers in spontaneously differentiating EBs. c. ChemiPS cells formed teratomas which displayed multiple tissues including ectoderm (neural tissue), mesoderm (cartilage and muscle), and endoderm (respiratory epithelium).
Figure 5B:
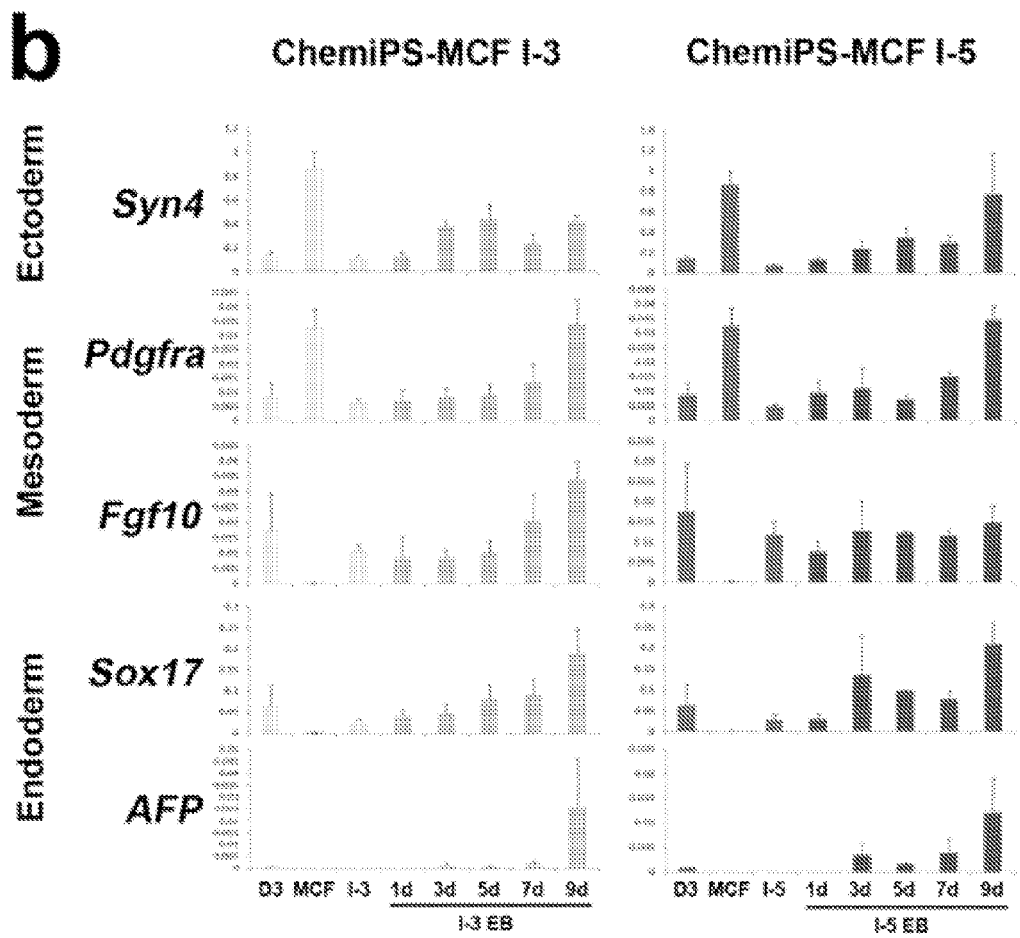

One property of both ES cells and iPS cells is their capability to form embryoid bodies (EBs) and differentiate into cell types of all three germ layers. To evaluate pluripotency in chemiPS cells in vitro, spontaneous differentiation to three germ layers by embryonic body (EB) formation assays were performed. To initiate EB formation, colonies were detached from the feeder layer with trypsin, and cell clusters plated in non-tissue-culture-treated plates followed by 9 day culture. Like mouse ES cells, chemiPS cells readily formed EBs at 9 days in suspension culture and spontaneously differentiated into cell types of all three embryonic germ layers as shown by immunostaining (FIG. 5A) and qRT-PCR (FIG. 5B).

Figure 5C:
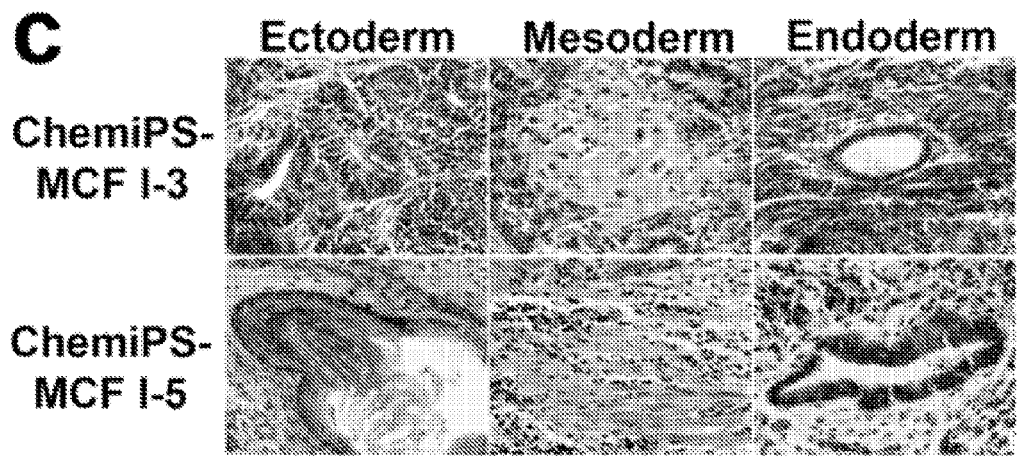

To determine the capacity of teratoma formation in vivo, a standard assay for pluripotency of ES cells, iPS cells were injected into the testes and back skins of immune-deficient mice (NOD/SCID). After 4 weeks, formation of encapsulated tumors were observed. Hematoxylin and eosin staining showed multiple tissues in tumors with characteristic clusters of tissues derived from all three embryonic germ layers indicating the formation of teratoma (FIG. 5C).

These results indicate that chemical induction can trigger the genetic reprogramming for pluripotency from somatic cells without using any genetic factor integrations and maintain the self-renewal for long period even when all chemical treatments are withdrawn.

Generation of Human iPS Cells Using Chemical Combinations

For PB-MNC isolation, peripheral blood will be drawn from volunteers under the protocol approved by the Emory University Institutional Review Board. The PB-MNCs will be fractionated by density gradient centrifugation with Histopaque-1077 (Sigma) at 400×g for 30 mins and will be seeded onto six well plates (Costar). After following the iPS generation protocol and selecting colonies showing typical morphology of ES cells, the cells will be maintained on mitomycin C-treated STO cells in ES medium consisting of DMEM/F-12 medium supplemented with 20% serum replacement (SR; Gibco), 1 mM L-glutamine, 1% nonessential amino acids, 0.1 mM (3-mercaptoethanol, 4 ng/mL bFGF (Sigma), and 1% penicillin-streptomycin. The fully-grown iPS cells will be mechanically isolated and transferred onto a prepared dish with fresh feeder cells. For spontaneous differentiation, ES cells or iPS cells will be cultured in ES medium without bFGF to form EBs. Ten days later, the EBs will be replated onto gelatin-coated plates in 10% FBS/DMEM for further culture. Human dermal fibroblasts (HDF)(Cell Application, Inc.) will be cultured in 10% fetal bovine serum (FBS)/DMEM (Gibco).

Ten to 15 days after treatment with various compounds, colonies showing hES-like morphology will be transferred onto STO cells. About twenty five (21-30) days after transduction, growing colonies will be mechanically dissociated to small clumps and transferred onto STO cells for further analysis. When using fibroblasts for reprogramming, HDF and HCF will be plated.

iPS cells and derivatives will be fixed with 4% paraformaldehyde for 20 mins and permeabilized with 0.1% Triton X-100 in PBS for 5 mins. After treatment with 1% normal goat serum for 30 mins at room temperature (RT), the cells will be incubated with human specific antibodies against OCT4 (1:200, Santa Cruz Biotechnology), and SSEA1, SSEA4, TRA-1-81, TRA-1-61, AFP, CD31, and NESTIN (all 1:200, Chemicon) for 24 hours at 4° C. After washes, bound primary antibodies will be detected with FITC (fluorescein isothiocyanate)-conjugated rabbit anti-mouse IgG (1:800, BD Bioscience) or Cy3-conjugated goat anti-mouse IgG (1:800, Molecular Probes Inc.) for 1 hour at RT. The stained slides will be washed and mounted with Vectashield mounting solution with DAPI (Vector Laboratories). For the alkaline phosphatase (AP) assay, cells will be fixed and activity of AP will be detected with an ES cell characterization kit (Chemicon). Images will be taken using an inverted fluorescence microscope (Olympus) (DXM1200C, Nikon).

What is claimed:
1. A composition comprising a compound having Formula II:

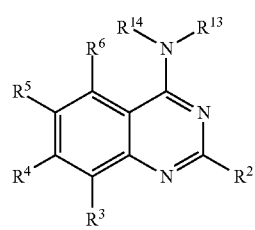

Formula II or salts thereof wherein,
$R^2$ is alkylamino or (alkyl)$_2$amino optionally substituted with one or more, the same or different, $R^7$;
$R^4$ is alkoxy optionally substituted with one or more, the same or different, $R^7$;
$R^3$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^3$, $R^5$, and $R^6$ are optionally substituted with one or more, the same or different, $R^7$;
$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkyl sulfinyl, alkyl sulfonyl, arylsulfonyl, carbocyclyl, aryl, or heterocyclyl, wherein $R^7$ is optionally substituted with one or more, the same or different, $R^8$;
$R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methyl sulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^{13}$ and $R^{14}$ are alkyl wherein each $R^{13}$ and $R^{14}$ are optionally substituted with one or more, the same or different, $R^{15}$;

$R^{15}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{15}$ is optionally substituted with one or more, the same or different, $R^{16}$; and $R^{16}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The composition of claim 1, wherein the compound is selected from:
7-((5-aminopentyl)oxy)-$N^2$-(3-(dimethylamino)propyl)-6-methoxy-$N^4$,$N^4$-dimethylquinazoline-2,4-diamine and
7-((5-aminopentyl)oxy)-6-methoxy-$N^2$,$N^2$,$N^4$,$N^4$-tetramethylquinazoline-2,4-diamine or salts thereof.

3. The composition of claim 1 further comprising a DNA methylation inhibitor, a histone deacetylase (HDAC) inhibitor, a Rho-associated kinase (ROCK) inhibitor, Wnt inhibitor, GSK-3beta inhibitor, or a dihydropyridine.

4. The composition of claim 3, wherein the DNA methylation inhibitor is 5-azacitidine or decitabine.

5. The composition of claim 3, wherein the HDAC inhibitor is vorinostat-suberoylanilide hydroxamic acid (SAHA), trichostatin A (TSA), or valproic acid (VPA).

6. The composition of claim 3, wherein the ROCK inhibitor is 4-(1-aminoethyl)-N-(pyridin-4-yl)cyclohexanecarboxamide (Y-27632) or salt thereof.

7. The composition of claim 3, wherein the dihydropyridine is 1,4-dihydro-2,6-dimethyl-5-nitro-4-[2-(trifluoromethyl)phenyl]-3-pyridinecarboxylic acid, methyl ester (BayK8644), ester, derivative, or salt thereof.

8. The composition of claim 3, wherein the GSK-3beta inhibitor is 6-[[2-[[4-(2,4-dichlorophenyl)-5-(5-methyl-1H-imidazol-2-yl)-2 pyrimidinyl]amino]ethyl]amino]-3-pyridinecarbonitrile (CHIR99201) or salt thereof.

9. The composition of claim 1, further comprising leukemia inhibitory factor (LIF), fibroblast growth factors (FGFs), MEK, or TGF-β.

10. A composition comprising a compound having Formula IA:

Formula I

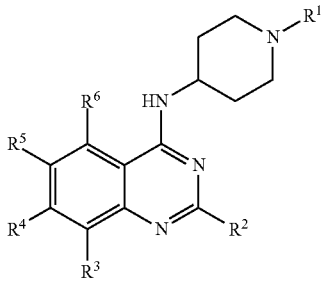

or salts thereof wherein, $R^1$, $R^3$, $R^4$, $R^5$, and $R^6$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^1$, $R^2$, $R^3$, $R^4$, $R^5$, and $R^6$ are optionally substituted with one or more, the same or different, $R^7$;

$R^7$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkyl sulfonyl, arylsulfonyl, carbocyclyl, aryl, or heterocyclyl, wherein $R^7$ is optionally substituted with one or more, the same or different, $R^8$;

$R^8$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl;

$R^9$ and $R^{10}$ are each the same or different hydrogen, alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein each $R^9$ and $R^{10}$ are optionally substituted with one or more, the same or different, $R^{11}$;

or $R^9$ and $R^{10}$ come together to form a heterocyclyl optionally substituted with one or more, the same or different, $R^{11}$;

$R^{11}$ is alkyl, halogen, nitro, cyano, hydroxy, amino, mercapto, formyl, carboxy, alkanoyl, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein is optionally substituted with one or more, the same or different, $R^{12}$; and $R^{12}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethyl sulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

11. The composition of claim 10, wherein the compounds are selected from:

$N^4$-(1-benzylpiperidin-4-yl)-$N^2$-(piperidin-1-yl)quinazoline-2,4-diamine, $N^4$-(1-benzylpiperidin-4-yl)-$N^2$-(4-methylpiperazin-1-yl)quinazoline-2,4-diamine, and $N^4$-(1-benzylpiperidin-4-yl)-$N^2$-morpholinoquinazoline-2,4-diamine, or salts thereof.

* * * * *